(12) United States Patent
Mahajan et al.

(10) Patent No.: US 7,034,117 B2
(45) Date of Patent: Apr. 25, 2006

(54) RAD51 POLYPEPTIDES AND USES THEREOF

(75) Inventors: Pramod B. Mahajan, Urbandale, IA (US); Jinrui Shi, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 35 days.

(21) Appl. No.: 10/818,809

(22) Filed: Apr. 6, 2004

(65) Prior Publication Data

US 2004/0172689 A1 Sep. 2, 2004

Related U.S. Application Data

(62) Division of application No. 09/537,654, filed on Mar. 29, 2000, now Pat. No. 6,720,478.

(60) Provisional application No. 60/132,582, filed on May 5, 1999.

(51) Int. Cl.
*C07K 1/00* (2006.01)
(52) U.S. Cl. ..................................................... 530/350
(58) Field of Classification Search ................ 530/350, 530/387.1; 512/14
See application file for complete search history.

(56) References Cited

U.S. PATENT DOCUMENTS 4,665,160 A * 5/1987 Seeburg ...................... 530/399
5,661,021 A * 8/1997 Buchert et al. ............. 435/209

FOREIGN PATENT DOCUMENTS

WO WO 97/41228 A3 11/1997

OTHER PUBLICATIONS

Rounsley et al, Jan. 1998, Putative DNA Repair Protein (RAD57).*
Reiss et al, RecA protein stimulates homologous recombination in plants, 1996, Proc. Natl. Acad., vol. 93, pp. 3094-3098.*
Reiss et al, "RecA stimulates sister chromatid exchange and the fidelity of double-strand break repair, but not gene targeting, in plants transformed by Agrobacterium", 2000, PNAS vol. 97 No. 7 pp. 3358-3363.*
Dosanjh et al, Isolation and characterization of RAD51C, a new human member of the RAD51 family of related genes, 1998, Nucleic Research, 1998, vol. 26 No. 5, pp. 1179-1184.*
Hill et al, Functional Analysis of Conserved Histidines in ADP-Glucose Proyphosphorylase from *Escherichia coli*, 1998, Biochemical and Biophysical Research Comm. vol. 244, pp. 573-577.*
Broun et al, Catalytic Plasticity of Fatty Acid Modification Enzymes Underlying chemical Diversity of Plant Lipids, 1998, Science vol. 282, pp. 1315-1317.*
Bowie e al, "Deciphering the Message in Protein Sequences: Tolerance to Amino Acid Substitutions", 1990, Science vol. 247, pp. 1306-1310.*
Gordon-Kamm, "Transformation of Maize Cells and Regeneration of Fertile Transgenic Plants", 1990, The Plant Cell. vol. 2, pp. 603-618.*
Lazar et al, Transforming Growth Factor x: Mutation of Aspartic Acid 47 and Leucine 48 Results in Different Biological Activies, 1988, Molecular and Cellular Biology vol. 8 No. 3, pp. 1247-1252.*
Shinohara et al., Homologous recombination and the roles of double-strand breaks, Trends in Biochem. Sci. 237:387-391 (1995).
Ogawa et al., Rec-A-like Recombination Proteins in Eukaryotes: Functions and Structures of RAD51 Genes, Cold Spring Harbor Symposia on Quantitative Biology, 58:567-576 (1993).
Johnson et al., Functional Differences and Interactions among the Putative RecA Homologs Rad51, Rad55, and Rad57, Mol. Cell. Biol. 15(9):4843-4850 (1995).
Kans et al., Nucleotide sequence of the RAD57 gene of *Saccharomyces cerevisiae*, Gene 105:139-140 (1991).
Jeggo, P.A., Identification of Genes Involved in Repair of DNA Double-Strand Breaks in Mammalian Cells, Radiation Research 150 (Suppl.) S80-S91 (1998).
Sung, P., Yeast Rad55 and Rad57 proteins form a heterodimer that functions with replication protein A to promote DNA strand exchange by Rad51 recombinase, Genes & Development 11:1111-1121 (1997).

(Continued)

*Primary Examiner*—Jon Weber
*Assistant Examiner*—Agnes Rooke
(74) *Attorney, Agent, or Firm*—Pioneer Hi-Bred International, Inc.

(57) ABSTRACT

The invention provides isolated RAD51C nucleic acids and their encoded proteins. The present invention provides methods and compositions relating to altering RAD51C levels in plants. The invention further provides recombinant expression cassettes, host cells, transgenic plants, and antibody compositions.

9 Claims, No Drawings

OTHER PUBLICATIONS

Sung, P., Catalysis of ATP-Dependent Homologous DNA Pairing and Strand Exchange by Yeast RAD51 Protein, Science 265:1241-1243 (1994).

Sung et al., DNA Strand Exchange Mediated by a RAD51-ssDNA Nucleoprotein Filament with Polarity Opposite to That of RecA, Cell 82:453-461 (1995).

Vispe et al., Mammalian Rad51 protein: A RecA homologue with pleiotropic functions, Biochimie 79:587-592 (1997).

Yoshimura et al., Cloning and sequence of the human RecA-like gene cDNA, Nuc. Acids Res. 21(7):1665 (1993).

Rice et al., Isolation of human and mouse genes based on homology to REC2, recombinational repair gene from the fungus Ustilago maydis, Proc. Natl. Acad. Sci. USA 94:7417-7422 (1997).

Albala et al., Identification of a Novel Human RAD51 Homolog, RAD51B, Genomics 46:476-479 (1997).

Dosanjh et al., Isolation and characterization of RAD51C, a new human member of the RAD 51 family of related genes, Nuc. Acids Res. 26(5):1179-1184 (1998).

Pittman et al., Identification, Characterization, and Genetic Mapping of Rad51d, A New Mouse and Human RAD51/RecA-Related Gene, Genoimics 49:103-111 (1998).

Tsuzuki et al., Targeted disruption of the Rad51 gene leads to lethality in embryonic mice, Proc. Natl. Acad. Sci. USA 93:6236-6240 (1996).

Xia et al., Elevated Recombination in Immortal Human Cells is Mediated by HsRAD51 Recombinase, Mol. Cell. Biol. 17(12):7151-7158 (1997).

Vispe et al., Overexpression of Rad51 protein stimulates homologous recombination and increases resistance of mammalian cells to ionizing radiation, Nuc. Acids Res. 26(12):2859-2864 (1998).

Lin et al., *Arabidopsis thaliana* chromosome II section 242 of 255 of the complete sequence. Sequence from clones T14P1, F4L23, EMBL Database Entry AC002387; Accession No. AC002387 (1999).

Thacker et al., A surfeit of RAD51-like genes, Trends in Genetics 15(5):166-168 (1999).

Shoemaker et al., Public Soybean EST Project; sf36d09.x1 Gm-c1028 Glycine max cDNA clone Genome Systems Clone ID: Gm-c1028-2058 3' similar to TR:O22144 O22144 Putative DNA Repair Protein; mRNA, EMB Database Entry AW310460; Accession No. AW310460 (2000).

* cited by examiner

```
                           SEQUENCE LISTING

<160> NUMBER OF SEQ ID NOS: 8

<210> SEQ ID NO 1
<211> LENGTH: 1474
<212> TYPE: DNA
<213> ORGANISM: Zea mays
<220> FEATURE:
<221> NAME/KEY: CDS
<222> LOCATION: (310)...(1192)

<400> SEQUENCE: 1
tcgacccacg cgtccgcact tgactcccag tctcccactg tgcgcagttc gcttggtccc      60
cggagcccca aaggcggcgg tgagccggag cccggagacg acgcgcggc gcgactcccc     120 cctaagcgac agcggcggcg tcgacgtaag cggctgcgtg gcgccaccga cggaggctac     180
gagcggttgt ggaggcagat atgagaggtg gaggtggcta caacgggtcg gcggctgtga     240
gatactgaaa tccgcactgc agttctcttc ttcccccaat cagtaccacc tctccaagtg     300 gcaatcacc atg gga gat caa tct ggc tct aga aat gga cca caa cag aag     351
           Met Gly Asp Gln Ser Gly Ser Arg Asn Gly Pro Gln Gln Lys
             1               5                  10 tac gtt tca gga gcc cag aat gcc tgg gat atg ttc tct gat gag ctg       399
Tyr Val Ser Gly Ala Gln Asn Ala Trp Asp Met Phe Ser Asp Glu Leu
 15                  20                  25                  30 tca cag aaa cac atc act act ggt tct ggt gac ctc aat gac ata ctt       447
Ser Gln Lys His Ile Thr Thr Gly Ser Gly Asp Leu Asn Asp Ile Leu
                 35                  40                  45 ggt ggc ggg att cac tgc aaa gaa gtt act gag atc ggt ggc gtc cca       495
```

```
Gly Gly Gly Ile His Cys Lys Glu Val Thr Glu Ile Gly Gly Val Pro
            50                  55                  60 ggg gtt ggt aaa act caa ctg ggg att caa cta gca atc aat gta caa    543
Gly Val Gly Lys Thr Gln Leu Gly Ile Gln Leu Ala Ile Asn Val Gln
        65                  70                  75 atc cca gtg gaa tgt ggt ggc ctt ggt ggg aaa gca gtt tat ata gat    591
Ile Pro Val Glu Cys Gly Gly Leu Gly Gly Lys Ala Val Tyr Ile Asp
    80                  85                  90 aca gag ggc agt ttc atg gtt gaa cgt gtc tac cag att gct gaa ggg    639
Thr Glu Gly Ser Phe Met Val Glu Arg Val Tyr Gln Ile Ala Glu Gly
95                  100                 105                 110 tgt att agg gac ata ctg gag cac ttt ccg cac agc cat gag aag tcc    687
Cys Ile Arg Asp Ile Leu Glu His Phe Pro His Ser His Glu Lys Ser
                115                 120                 125 tct tct gtc caa aaa caa tta cag cct gag cgt ttc ctg gcg gat atc    735
Ser Ser Val Gln Lys Gln Leu Gln Pro Glu Arg Phe Leu Ala Asp Ile
            130                 135                 140 tat tac ttc cgg ata tgc agt tac acc gaa caa att gca gtc ata aac    783
Tyr Tyr Phe Arg Ile Cys Ser Tyr Thr Glu Gln Ile Ala Val Ile Asn
        145                 150                 155 tac atg gag aag ttc ctc aga gag cat aaa gat gtg cgt ata gtt att    831
Tyr Met Glu Lys Phe Leu Arg Glu His Lys Asp Val Arg Ile Val Ile
    160                 165                 170 att gat agt gtt act ttc cac ttt cga caa gat ttt gaa gat ctg gca    879
Ile Asp Ser Val Thr Phe His Phe Arg Gln Asp Phe Glu Asp Leu Ala
175                 180                 185                 190 ctg agg acc aga gtg cta agt gga tta tca ttg aag tta atg aag att    927
Leu Arg Thr Arg Val Leu Ser Gly Leu Ser Leu Lys Leu Met Lys Ile
                195                 200                 205 gca aag aca tat aac ttg gca gtt gtc ttg ttg aac caa gtc act act    975
Ala Lys Thr Tyr Asn Leu Ala Val Val Leu Leu Asn Gln Val Thr Thr
            210                 215                 220 aaa ttt aca gaa ggg tca ttt caa ttg act ctt gct cta ggt gac agc   1023
Lys Phe Thr Glu Gly Ser Phe Gln Leu Thr Leu Ala Leu Gly Asp Ser
        225                 230                 235 tgg tcc cac tca tgc acg aac cgg ttg att ctg cac tgg aat ggg aac   1071
Trp Ser His Ser Cys Thr Asn Arg Leu Ile Leu His Trp Asn Gly Asn
    240                 245                 250 gaa cga tac gca cat ctt gat aag tct cct tca ctt cca gta gcc tca   1119
Glu Arg Tyr Ala His Leu Asp Lys Ser Pro Ser Leu Pro Val Ala Ser
255                 260                 265                 270 gca ccg tat gca gtg aca ggc aaa ggg att aga gat gct gtg agc tca   1167
Ala Pro Tyr Ala Val Thr Gly Lys Gly Ile Arg Asp Ala Val Ser Ser
                275                 280                 285 aac cac aag cga gcc cga gta acg t agcattcttg gtgtcaagca            1212
Asn His Lys Arg Ala Arg Val Thr
            290 cttgtatgtc cactacgctc ctgcagcttt cttcgccatg gatcttttgg actagtgagg  1272 tgagactgga gaatagtacc attttgttga ttctcagttg ctttgtgccg ttggctacca  1332 accaacctta agagagaagt aaatacaaca gaacaggcta atatagtgtt ttgtatctga  1392 acatctggcc catcgtacat tcagtaaagc ctataatagc gggcaaaaaa aaaaaaaaaa  1452 aaaaaaaaaa aaaaaaaaaa aa                                          1474

<210> SEQ ID NO 2
<211> LENGTH: 294
<212> TYPE: PRT
<213> ORGANISM: Zea mays
```

<400> SEQUENCE: 2

```
Met Gly Asp Gln Ser Gly Ser Arg Asn Gly Pro Gln Gln Lys Tyr Val
 1               5                  10                  15
Ser Gly Ala Gln Asn Ala Trp Asp Met Phe Ser Asp Glu Leu Ser Gln
            20                  25                  30
Lys His Ile Thr Thr Gly Ser Gly Asp Leu Asn Asp Ile Leu Gly Gly
        35                  40                  45
Gly Ile His Cys Lys Glu Val Thr Glu Ile Gly Val Pro Gly Val
    50                  55                  60
Gly Lys Thr Gln Leu Gly Ile Gln Leu Ala Ile Asn Val Gln Ile Pro
65                  70                  75                  80
Val Glu Cys Gly Gly Leu Gly Gly Lys Ala Val Tyr Ile Asp Thr Glu
                85                  90                  95
Gly Ser Phe Met Val Glu Arg Val Tyr Gln Ile Ala Glu Gly Cys Ile
            100                 105                 110
Arg Asp Ile Leu Glu His Phe Pro His Ser His Glu Lys Ser Ser Ser
        115                 120                 125
Val Gln Lys Gln Leu Gln Pro Glu Arg Phe Leu Ala Asp Ile Tyr Tyr
    130                 135                 140
Phe Arg Ile Cys Ser Tyr Thr Glu Gln Ile Ala Val Ile Asn Tyr Met
145                 150                 155                 160
Glu Lys Phe Leu Arg Glu His Lys Asp Val Arg Ile Val Ile Ile Asp
                165                 170                 175
Ser Val Thr Phe His Phe Arg Gln Asp Phe Glu Asp Leu Ala Leu Arg
            180                 185                 190
Thr Arg Val Leu Ser Gly Leu Ser Leu Lys Leu Met Lys Ile Ala Lys
        195                 200                 205
Thr Tyr Asn Leu Ala Val Val Leu Leu Asn Gln Val Thr Thr Lys Phe
    210                 215                 220
Thr Glu Gly Ser Phe Gln Leu Thr Leu Ala Leu Gly Asp Ser Trp Ser
225                 230                 235                 240
His Ser Cys Thr Asn Arg Leu Ile Leu His Trp Asn Gly Asn Glu Arg
                245                 250                 255
Tyr Ala His Leu Asp Lys Ser Pro Ser Leu Pro Val Ala Ser Ala Pro
            260                 265                 270
Tyr Ala Val Thr Gly Lys Gly Ile Arg Asp Ala Val Ser Ser Asn His
        275                 280                 285
Lys Arg Ala Arg Val Thr
    290
```

<210> SEQ ID NO 3
<211> LENGTH: 1459
<212> TYPE: DNA
<213> ORGANISM: Zea mays
<220> FEATURE:
<221> NAME/KEY: CDS
<222> LOCATION: (169)...(1011)

<400> SEQUENCE: 3

```
cgacgtaagc ggctgcgtgg cgccaccgac ggaggctacg agcggttgtg gaggcagata    60
tgagaggtgg aggtggctac aacgggtcgg cggctgtgag atactgaaat ccgcactgca   120
gttctcttct tcccccaatc agtaccacct ctccaagtgg caatcacc atg gga gat   177
                                                    Met Gly Asp
                                                     1
caa tct ggc tct aga aat gga cca caa cag aag tac gtt tca gga gcc   225
```

|  |  |  |  |  |  |  |  |  |  |  |  |  |  |  |
|---|---|---|---|---|---|---|---|---|---|---|---|---|---|---|
| Gln | Ser | Gly | Ser | Arg | Asn | Gly | Pro | Gln | Gln | Lys | Tyr | Val | Ser | Gly | Ala |
|  | 5 |  |  |  | 10 |  |  |  |  | 15 |  |  |  |  |

```
cag aat gcc tgg gat atg ttc tct gat gag ctg tca cag aaa cac atc      273
Gln Asn Ala Trp Asp Met Phe Ser Asp Glu Leu Ser Gln Lys His Ile
 20              25                  30                  35 act act ggt tct ggt gac ctc aat gac ata ctt ggt ggc ggg att cac      321
Thr Thr Gly Ser Gly Asp Leu Asn Asp Ile Leu Gly Gly Gly Ile His
             40                  45                  50 tgc aaa gaa gtt act gag atc ggt ggc gtc cca ggg gtt ggt aaa act      369
Cys Lys Glu Val Thr Glu Ile Gly Gly Val Pro Gly Val Gly Lys Thr
                 55                  60                  65 caa ctg ggg att caa cta gca atc aat gta caa atc cca gtg gaa tgt      417
Gln Leu Gly Ile Gln Leu Ala Ile Asn Val Gln Ile Pro Val Glu Cys
         70                  75                  80 ggt ggc ctt ggt ggg aaa gca gtt tat ata gag ggc agt ttc atg gtt      465
Gly Gly Leu Gly Gly Lys Ala Val Tyr Ile Glu Gly Ser Phe Met Val
     85                  90                  95 gaa cgt gtc tac cag att gct gaa ggg tgt att agg gac ata ctg gag      513
Glu Arg Val Tyr Gln Ile Ala Glu Gly Cys Ile Arg Asp Ile Leu Glu
100                 105                 110                 115 cac ttt ccg cac agc cat gag aag tcc tct tct gtc caa aaa caa tta      561
His Phe Pro His Ser His Glu Lys Ser Ser Ser Val Gln Lys Gln Leu
                 120                 125                 130 cag cct gag cgt ttc ctg gcg gat atc tat tac ttc cgg ata tgc agt      609
Gln Pro Glu Arg Phe Leu Ala Asp Ile Tyr Tyr Phe Arg Ile Cys Ser
             135                 140                 145 tac acc gaa caa att gca gtc ata aac tac atg gag aag ttc ctc aga      657
Tyr Thr Glu Gln Ile Ala Val Ile Asn Tyr Met Glu Lys Phe Leu Arg
         150                 155                 160 gag cat aaa gat gtg cgt ata gtt att att gat agt gtt act ttc cac      705
Glu His Lys Asp Val Arg Ile Val Ile Ile Asp Ser Val Thr Phe His
     165                 170                 175 ttt cga caa gat ttt gaa gat ctg gca ctg agg acc aga gtg cta agt      753
Phe Arg Gln Asp Phe Glu Asp Leu Ala Leu Arg Thr Arg Val Leu Ser
180                 185                 190                 195 gga tta tca ttg aag tta atg aag att gca aag aca tat aac ttg gca      801
Gly Leu Ser Leu Lys Leu Met Lys Ile Ala Lys Thr Tyr Asn Leu Ala
                 200                 205                 210 gtt gtc ttg ttg aac caa gtc act act aaa ttt aca gaa ggg tca ttt      849
Val Val Leu Leu Asn Gln Val Thr Thr Lys Phe Thr Glu Gly Ser Phe
             215                 220                 225 caa ttg act ctt gct cta ggt gac agc tgg tcc cac tca tgc acg aac      897
Gln Leu Thr Leu Ala Leu Gly Asp Ser Trp Ser His Ser Cys Thr Asn
         230                 235                 240 cgg ttg att ctg cac tgg aat ggg aac gaa cga tac gca cat ctt gat      945
Arg Leu Ile Leu His Trp Asn Gly Asn Glu Arg Tyr Ala His Leu Asp
     245                 250                 255 aag tct cct tca ctt cca gta gcc tca gcc ccg tat gca gtg aca ggc      993
Lys Ser Pro Ser Leu Pro Val Ala Ser Ala Pro Tyr Ala Val Thr Gly
260                 265                 270                 275 aaa ggg att aga gat gtg tgagctcaaa ccacaagcga gcccgagtaa            1041
Lys Gly Ile Arg Asp Val
                 280 cgtagcattc ttggtgtcaa gcacttgtat gtccactacg ctcctgcagc tttcttcgcc   1101 atggatcttt tggactagtg aggtgagact ggagaatagt accatttgat tctcagttgc   1161 tttgtgccgt tggctaccaa ccaaccttaa gagagaagta aatacaacag aacaggctaa   1221 tatagtgttt tgtatctgaa catctggccc atcgtacatt cagtaaagcc tataatagcg   1281
```
ggcatatatg tgcttctctg atcaccgatc agcaaaaaaa aaaaaaaaaa aaaaaaaaaa 1341 aaaaaaaaaa aaaaaaaaaa aaaaaaaaaa aaaaaaaaaa aaaaaaaaaa aaaaaaaaaa 1401 aaaaaaaaaa aaaaaaaaaa aaaaaaaaaa aaaaaaaaaa aaaaaaaaaa aaaaaaa 1459

<210> SEQ ID NO 4
<211> LENGTH: 281
<212> TYPE: PRT
<213> ORGANISM: Zea mays

<400> SEQUENCE: 4

Met Gly Asp Gln Ser Gly Ser Arg Asn Gly Pro Gln Gln Lys Tyr Val
1               5                   10                  15

Ser Gly Ala Gln Asn Ala Trp Asp Met Phe Ser Asp Glu Leu Ser Gln
            20                  25                  30

Lys His Ile Thr Thr Gly Ser Gly Asp Leu Asn Asp Ile Leu Gly Gly
        35                  40                  45

Gly Ile His Cys Lys Glu Val Thr Glu Ile Gly Val Pro Gly Val
    50                  55                  60

Gly Lys Thr Gln Leu Gly Ile Gln Leu Ala Ile Asn Val Gln Ile Pro
65                  70                  75                  80

Val Glu Cys Gly Gly Leu Gly Gly Lys Ala Val Tyr Ile Glu Gly Ser
                85                  90                  95

Phe Met Val Glu Arg Val Tyr Gln Ile Ala Glu Gly Cys Ile Arg Asp
            100                 105                 110

Ile Leu Glu His Phe Pro His Ser His Glu Lys Ser Ser Val Gln
        115                 120                 125

Lys Gln Leu Gln Pro Glu Arg Phe Leu Ala Asp Ile Tyr Tyr Phe Arg
130                 135                 140

Ile Cys Ser Tyr Thr Glu Gln Ile Ala Val Ile Asn Tyr Met Glu Lys
145                 150                 155                 160

Phe Leu Arg Glu His Lys Asp Val Arg Ile Val Ile Asp Ser Val
                165                 170                 175

Thr Phe His Phe Arg Gln Asp Phe Glu Asp Leu Ala Leu Arg Thr Arg
            180                 185                 190

Val Leu Ser Gly Leu Ser Leu Lys Leu Met Lys Ile Ala Lys Thr Tyr
        195                 200                 205

Asn Leu Ala Val Val Leu Leu Asn Gln Val Thr Thr Lys Phe Thr Glu
    210                 215                 220

Gly Ser Phe Gln Leu Thr Leu Ala Leu Gly Asp Ser Trp Ser His Ser
225                 230                 235                 240

Cys Thr Asn Arg Leu Ile Leu His Trp Asn Gly Asn Glu Arg Tyr Ala
                245                 250                 255

His Leu Asp Lys Ser Pro Ser Leu Pro Val Ala Ser Ala Pro Tyr Ala
            260                 265                 270

Val Thr Gly Lys Gly Ile Arg Asp Val
        275                 280

<210> SEQ ID NO 5
<211> LENGTH: 1333
<212> TYPE: DNA
<213> ORGANISM: Zea mays
<220> FEATURE:
<221> NAME/KEY: CDS
<222> LOCATION: (169)...(1050)

<400> SEQUENCE: 5

-continued

| | |
|---|---|
| cgacgtaagc ggctgcgtgg cgccaccgac ggaggctacg agcggttgtg gaggcagata | 60 |
| tgagaggtgg aggtggctac aacgggtcgg cggctgtgag atactgaaat ccgcactgca | 120 |
| gttctcttct tcccccaatc agtaccacct ctccaagtgg caatcacc atg gga gat<br>                               Met Gly Asp<br>                                1 | 177 |
| caa tct ggc tct aga aat gga cca caa cag aag tac gtt tca gga gcc<br>Gln Ser Gly Ser Arg Asn Gly Pro Gln Gln Lys Tyr Val Ser Gly Ala<br> 5        10        15 | 225 |
| cag aat gcc tgg gat atg ttc tct gat gag ctg tca cag aaa cac atc<br>Gln Asn Ala Trp Asp Met Phe Ser Asp Glu Leu Ser Gln Lys His Ile<br>20        25        30        35 | 273 |
| act act ggt tct ggt gac ctc aat gac ata ctt ggt ggc ggg att cac<br>Thr Thr Gly Ser Gly Asp Leu Asn Asp Ile Leu Gly Gly Gly Ile His<br>        40        45        50 | 321 |
| tgc aaa gaa gtt act gag atc ggt ggc gtc cca ggg gtt ggt aaa act<br>Cys Lys Glu Val Thr Glu Ile Gly Gly Val Pro Gly Val Gly Lys Thr<br>     55        60        65 | 369 |
| caa ctg ggg att caa cta gca atc aat gta caa atc cca gtg gaa tgt<br>Gln Leu Gly Ile Gln Leu Ala Ile Asn Val Gln Ile Pro Val Glu Cys<br>   70        75        80 | 417 |
| ggt ggc ctt ggt ggg aaa gca gtt tat ata gat aca gag ggc agt ttc<br>Gly Gly Leu Gly Gly Lys Ala Val Tyr Ile Asp Thr Glu Gly Ser Phe<br>85        90        95 | 465 |
| atg gtt gaa cgt gtc tac cag att gct gaa ggg tgt att agg gac ata<br>Met Val Glu Arg Val Tyr Gln Ile Ala Glu Gly Cys Ile Arg Asp Ile<br>100        105        110        115 | 513 |
| ctg gag cac ttt ccg cac agc cat gag aag tcc tct tct gtc caa aaa<br>Leu Glu His Phe Pro His Ser His Glu Lys Ser Ser Ser Val Gln Lys<br>        120        125        130 | 561 |
| caa tta cag cct gag cgt ttc ctg gcg gat atc tat tac ttc cgg ata<br>Gln Leu Gln Pro Glu Arg Phe Leu Ala Asp Ile Tyr Tyr Phe Arg Ile<br>     135        140        145 | 609 |
| tgc agt tac acc gaa caa att gca gtc ata aac tac atg gag aag ttc<br>Cys Ser Tyr Thr Glu Gln Ile Ala Val Ile Asn Tyr Met Glu Lys Phe<br>  150        155        160 | 657 |
| ctc aga gag cat aaa gat gtg cgt ata gtt att att gat agt gtt act<br>Leu Arg Glu His Lys Asp Val Arg Ile Val Ile Ile Asp Ser Val Thr<br>165        170        175 | 705 |
| ttc cac ttt cga caa gat ttt gaa gat ctg gca ctg agg acc aga gtg<br>Phe His Phe Arg Gln Asp Phe Glu Asp Leu Ala Leu Arg Thr Arg Val<br>180        185        190        195 | 753 |
| cta agt gga tta tca ttg aag tta atg aag att gca aag aca tat aac<br>Leu Ser Gly Leu Ser Leu Lys Leu Met Lys Ile Ala Lys Thr Tyr Asn<br>     200        205        210 | 801 |
| ttg gca gtt gtc ttg ttg aac caa gtc act act aaa ttt aca gaa ggg<br>Leu Ala Val Val Leu Leu Asn Gln Val Thr Thr Lys Phe Thr Glu Gly<br>  215        220        225 | 849 |
| tca ttt caa ttg act ctt gct cta ggt gac agc tgg tcc cac tca tgc<br>Ser Phe Gln Leu Thr Leu Ala Leu Gly Asp Ser Trp Ser His Ser Cys<br>   230        235        240 | 897 |
| acg aac cgg ttg att ctg cac tgg aat ggg aac gaa cga tac gca cat<br>Thr Asn Arg Leu Ile Leu His Trp Asn Gly Asn Glu Arg Tyr Ala His<br>245        250        255 | 945 |
| ctt gat aag tct cct tca ctt cca gta gcc tca gca ccg tat gca gtg<br>Leu Asp Lys Ser Pro Ser Leu Pro Val Ala Ser Ala Pro Tyr Ala Val<br>260        265        270        275 | 993 |
| aca ggc aaa ggg att aga gat gct gtg agc tca aac cac aag cga gcc<br>Thr Gly Lys Gly Ile Arg Asp Ala Val Ser Ser Asn His Lys Arg Ala<br>     280        285        290 | 1041 |

```
cga gta acg tagcattctt ggtgtcaagc acttgtatgt ccactacgct        1090
Arg Val Thr cctgctgctt tcttcgccat ggatcttttg gactagtgag gtgagactgg agaatagtac        1150
cattttgttg attctcagtt gctttgtgcc gttggctacc aaccaacctt aagagagaag        1210
taaatacaac agaacaggct aatatagtgt tttgtatctg aacatctggs ccatcgtaca        1270
ttcagtaaag cctataatag cgggcatata tgtgcttctc tgatcaaaaa aaaaaaaaaa        1330
aaa        1333
```

<210> SEQ ID NO 6
<211> LENGTH: 294
<212> TYPE: PRT
<213> ORGANISM: Zea mays

<400> SEQUENCE: 6

```
Met Gly Asp Gln Ser Gly Ser Arg Asn Gly Pro Gln Gln Lys Tyr Val
  1               5                  10                  15

Ser Gly Ala Gln Asn Ala Trp Asp Met Phe Ser Asp Glu Leu Ser Gln
             20                  25                  30

Lys His Ile Thr Thr Gly Ser Gly Asp Leu Asn Asp Ile Leu Gly Gly
         35                  40                  45

Gly Ile His Cys Lys Glu Val Thr Glu Ile Gly Val Pro Gly Val
     50                  55                  60

Gly Lys Thr Gln Leu Gly Ile Gln Leu Ala Ile Asn Val Gln Ile Pro
 65                  70                  75                  80

Val Glu Cys Gly Gly Leu Gly Gly Lys Ala Val Tyr Ile Asp Thr Glu
                 85                  90                  95

Gly Ser Phe Met Val Glu Arg Val Tyr Gln Ile Ala Glu Gly Cys Ile
            100                 105                 110

Arg Asp Ile Leu Glu His Phe Pro His Ser His Glu Lys Ser Ser Ser
        115                 120                 125

Val Gln Lys Gln Leu Gln Pro Glu Arg Phe Leu Ala Asp Ile Tyr Tyr
    130                 135                 140

Phe Arg Ile Cys Ser Tyr Thr Glu Gln Ile Ala Val Ile Asn Tyr Met
145                 150                 155                 160

Glu Lys Phe Leu Arg Glu His Lys Asp Val Arg Ile Val Ile Asp
                165                 170                 175

Ser Val Thr Phe His Phe Arg Gln Asp Phe Glu Asp Leu Ala Leu Arg
            180                 185                 190

Thr Arg Val Leu Ser Gly Leu Ser Leu Lys Leu Met Lys Ile Ala Lys
        195                 200                 205

Thr Tyr Asn Leu Ala Val Val Leu Leu Asn Gln Val Thr Thr Lys Phe
    210                 215                 220

Thr Glu Gly Ser Phe Gln Leu Thr Leu Ala Leu Gly Asp Ser Trp Ser
225                 230                 235                 240

His Ser Cys Thr Asn Arg Leu Ile Leu His Trp Asn Gly Asn Glu Arg
                245                 250                 255

Tyr Ala His Leu Asp Lys Ser Pro Ser Leu Pro Val Ala Ser Ala Pro
            260                 265                 270

Tyr Ala Val Thr Gly Lys Gly Ile Arg Asp Ala Val Ser Ser Asn His
        275                 280                 285

Lys Arg Ala Arg Val Thr
    290
```

-continued

<210> SEQ ID NO 7
<211> LENGTH: 36
<212> TYPE: DNA
<213> ORGANISM: Artificial Sequence
<220> FEATURE:
<223> OTHER INFORMATION: Designed oligonucleotide based upon an adaptor
      used for cDNA library construction and poly(dT) to
      remove clones which have a poly(A) tail but no
      cDNA insert.

<400> SEQUENCE: 7
tcgacccacg cgtccgaaaa aaaaaaaaaa aaaaaa                                     36

<210> SEQ ID NO 8
<211> LENGTH: 332
<212> TYPE: PRT
<213> ORGANISM: Arabidopsis thaliana

<400> SEQUENCE: 8

Met Ile Ser Phe Gly Arg Arg Lys Ser Pro Ala Ile Glu Glu Thr Ser
 1               5                  10                  15

Leu Ala Thr Ser Val Met Glu Ala Trp Arg Leu Pro Leu Ser Pro Ser
            20                  25                  30

Ile Arg Gly Lys Leu Ile Ser Ala Gly Tyr Thr Cys Leu Ser Ser Ile
        35                  40                  45

Ala Ser Val Ser Ser Ser Asp Leu Ala Arg Ala Lys Asn Ala Trp Asp
    50                  55                  60

Met Leu His Glu Glu Ser Leu Pro Arg Ile Thr Thr Ser Cys Ser
65                  70                  75                  80

Asp Leu Asp Asn Ile Leu Gly Gly Gly Ile Ser Cys Arg Asp Val Thr
                85                  90                  95

Glu Ile Gly Gly Val Pro Gly Ile Gly Lys Thr Gln Ile Gly Ile Gln
            100                 105                 110

Leu Ser Val Asn Val Gln Ile Pro Arg Glu Cys Gly Leu Gly Gly
        115                 120                 125

Lys Ala Ile Tyr Ile Asp Thr Glu Gly Ser Phe Met Val Glu Arg Ala
    130                 135                 140

Leu Gln Ile Ala Glu Ala Cys Val Glu Asp Met Glu Glu Tyr Thr Gly
145                 150                 155                 160

Tyr Met His Lys His Phe Gln Ala Asn Gln Val Gln Met Lys Pro Glu
                165                 170                 175

Asp Ile Leu Glu Asn Ile Phe Tyr Phe Arg Val Cys Ser Tyr Thr Glu
            180                 185                 190

Gln Ile Ala Leu Val Asn His Leu Glu Lys Phe Ile Ser Glu Asn Lys
        195                 200                 205

Asp Val Val Ile Val Asp Ser Ile Thr Phe His Phe Arg Gln Asp
    210                 215                 220

Tyr Asp Asp Leu Ala Gln Arg Thr Arg Val Leu Ser Glu Met Ala Leu
225                 230                 235                 240

Lys Phe Met Lys Leu Ala Lys Lys Phe Ser Leu Ala Val Val Leu Leu
                245                 250                 255

Asn Gln Val Thr Thr Lys Phe Ser Glu Gly Ser Phe Gln Leu Ala Leu
            260                 265                 270

Ala Leu Gly Asp Ser Trp Ser His Ser Cys Thr Asn Arg Val Ile Leu
        275                 280                 285

Tyr Trp Asn Gly Asp Glu Arg Tyr Ala Tyr Ile Asp Lys Ser Pro Ser
    290                 295                 300

```
-continued

Leu Pro Ser Ala Ser Ala Ser Tyr Thr Val Thr Ser Arg Gly Leu Arg
305                 310                 315                 320

Asn Ser Ser Ser Ser Lys Arg Val Lys Met Met
                325             330
```

RAD51 POLYPEPTIDES AND USES THEREOF

CROSS-REFERENCE TO RELATED APPLICATIONS

This application is a divisional of U.S. application Ser. No. 09/537,654 filed Mar. 29, 2000, now U.S. Pat. No. 6,720,478, and U.S. Application Ser. No. 60/132,582 filed May 5, 1999, both of which are herein incorporated by reference.

TECHNICAL FIELD

The present invention relates generally to plant molecular biology. More specifically, it relates to nucleic acids and methods for modulating their expression in plants.

BACKGROUND OF THE INVENTION

Cellular DNA undergoes double strand breakage during the course of many physiological events as well as in response to a variety of environmental insults (Friedburg, E., Walker, G. & Siede, W., *DNA Repair and Mutagenesis*, ASM Press, Washington DC, 1995; Nickollof, J. & Hoekstra, M., *DNA Damage and Repair*, Humana Press, Totowa, N.J., 1998). Left unrepaired, such double strand breaks (DSBs) lead to mutations that may prove lethal to the organism. Therefore, these DSBs are repaired promptly via two independent pathways: i) homologous recombination; or ii) non-homologous end joining (Friedburg, E., Walker, G. & Siede, W., *DNA Repair and Mutagenesis*, ASM Press, Washington D.C., 1995; Nickollof, J. & Hoekstra, M., *DNA Damage and Repair*, Humana Press, Totowa, N.J., 1998).

The first pathway involves a series of very specific biochemical reactions catalyzed by a complex of cellular proteins (Shinohara & Ogawa, *Trends in Biochem. Sci.* 237: 387–391, 1995). Due to the large number of proteins involved in this complex, it is referred to as a 'recombinosome' (Hays et al., *Proc. Natl. Acad. Sci. USA* 92: 6925–6929, 1995). This pathway is the dominant mode of DSB repair in lower eukaryotes such as yeast (Nickollof, J. & Hoekstra, M., *DNA Damage and Repair*, Humana Press, Totowa, N.J., 1998). Therefore, yeast has been used as a model eukaryote to study the biochemical and molecular details of the double strand break repair. RAD51 is one of the genes of the RAD52 epistasis group that is involved in this pathway. This gene encodes a protein (Rad51) of about 38 kDa. Rad51 is a structural and functional homologue of the bacterial recombinase enzyme (also known as RecA).

Because of the crucial role of double strand break repair pathways in maintaining genomic stability, they have been found to be conserved throughout evolution. Consequently, RAD51 homologues have been discovered and characterized from many animal and plant sources (reviewed by Ogawa et al. *In Cold Spring Harbor Symp. On Quant. Biol.*, Vol. LVIII pp. 567–576, 1993). Moreover, many eukaryotes have multiple forms of the RAD51 gene. The RAD51 family also includes structurally and functionally related genes such as DMC1, LIM15, RAD55 and RAD57. DMC1 has been implicated in meiotic recombination and associated double strand breaks (reviewed by Ogawa et al. *In Cold Spring Harbor Symp. On Quant Biol.*, Vol. LVIII pp. 567–576, 1993).

All the members of the RAD51 family and their bacterial counterpart (RecA) share an important structural motif known as the 'RecA signature sequence' or Domain II. This sequence forms the ATP binding sites, an important property of all these proteins. However, the eukaryotic members of the RAD51 family can be distinguished from the bacterial RecA protein by the presence of an N-terminal extension present only in the RAD51 family members and a C-terminal extension of about 100 amino acids that is present in RecA but not in RAD51 family members. Important differences also exist in the primary structure of eukaryotic RAD51, and other closely related genes such as RAD55 and RAD57, indicating different physiological roles for each of these genes (Johnson, R. D. & Symington, L. S., *Mol. Cell. Biol.* 15: 4843–4850, 1995). It has been suggested that protein products of RAD55 and RAD57 genes interact with the RAD51 gene product during double strand break repair and recombination. The RAD57 gene of the budding yeast *Saccharomyces cerevisiae* also belongs to the RAD52 epistasis group (Kans, J. & Mortimer, R. Gene 105: 139–140, 1991). All members of this group are required for double strand break repair and genetic recombination. The RAD57 gene encodes a protein (Rad57) which shows significant homology to bacterial RecA and the eukaryotic counterpart, the Rad51 protein (Jeggo, P. Radiat Res. 150: S80–S91, 1998). Specifically, the ATP-binding motif (Walker Box A) is conserved in all the known Rad57 sequences (Hays, S. et al. *Proc. Natl. Acad. Sci.* 92: 6925–6929, 1995). Functional analysis has revealed interactions of Rad57 with Rad51, Rad52 and Rad55 to form a 'recombinosome' (Johnson, R. et al., *Mol. Cell. Biol.* 15: 4843–4850, 1995). Furthermore, in yeast, the Rad57-Rad55 heterodimer markedly stimulates DNA strand exchange by Rad51 (Sung P. *Genes Develop.* 11: 111–1121, 1997).

Biochemical studies have established that Rad51 catalyzes the strand exchange reaction between a circular ssDNA and linear dsDNA in presence of ATP and $Mg^{+2}$ ions (Sung, P. *Science* 265: 1241–1243, 1994; Sung, P. & Robberson, D. L. *Cell* 82: 453–461, 1995). These properties are very similar to RecA. However, unlike the bacterial protein, strand exchange by Rad51 is slower and requires the presence of 3' and 5' overhangs that are complementary. Rad51 does not promote joint molecule formation if the linear DNA has blunt or recessed complementary ends. As a consequence of this requirement for the presence of overhangs, the Rad51 catalyzed strand exchange reaction has a polarity (Sung, P. *Science* 265: 1241–1243, 1994; Sung, P. & Robberson, D. L. *Cell* 82: 453–461, 1995). Also, whereas RecA binds to ssDNA or partially single-stranded DNA, Rad51 shows similar binding affinity for ssDNA and dsDNA. These biochemical observations, coupled with extensive genetic studies indicate the involvement of additional proteins in the eukaryotic recombination and double strand repair reactions.

Recent studies have uncovered several RAD51 genes in higher eukaryotes (Vispe, S. & Defais, M., *Biochimie* 79: 587–592, 1997). For example, at least four human RAD51 genes, RAD51 (Yoshimura, Y., et al., *Mol. Cell. Biol.* 21, 1665.), RAD51B/REC2 (Rice, M. C., et al., *Proc. Natl. Acad. Sci.* 94: 7417–7422; Albala, J. S., et al., *Genomics* 46, 476–479, 1998), RAD51C (Dosanjh, M., et al., *Nucleic Acid Res.* 26: 1179–1184, 1998), and RAD51D (Pittman, D. et al., 49: 103–111, 1998) have been cloned and characterized.

Existence of multiple isoforms of RAD51 gene products in higher eukaryotes suggests their differential functional role in meiotic versus mitotic recombination. Interestingly, while the yeast RAD51 is not an essential gene, the mouse RAD51 null mutations are embryonic lethal (Tsuzuki, T., et al., *Proc. Natl. Acad. Sci.* 93: 6236–6240, 1996). Biochemical and genetic analyses of different orthologs of RAD51 (preferably from the same species) will shed light on their precise functions. Nonetheless, two very recent studies have clearly established that overexpression of Rad51 protein stimulates homologous recombination and increases resistance to ionizing radiation in immortalized human cells (Xia, S. et al., *Mol. Cell. Biol.* 17: 7151–7158, 1997) and Chinese hamster cells (Vispe, S., et al., *Nucleic Acid Res.* 26: 2859–2864, 1998).

In view of the central role of RAD51 gene products in recombination and double strand repair, RAD51 genes from maize find use as a tool for improving maize transformation in general and maize gene targeting in particular. The present invention describes full-length cDNAs for a novel maize ortholog of RAD51, which shows high homology to the human RAD51C gene.

Control of homologous recombination by modulating RAD51 provides the means to modulate the efficiency with which nucleic acids of interest are incorporated into the genomes of a target plant cell. Control of these processes has important implications in the creation of novel recombinantly engineered crops such as maize. The present invention provides this and other advantages.

SUMMARY OF THE INVENTION

Generally, it is the object of the present invention to provide nucleic acids and proteins relating to maize Rad51. It is an object of the present invention to provide: 1) antigenic fragments of the proteins of the present invention; 2) transgenic plants comprising the nucleic acids of the present invention; 3) methods for modulating, in a transgenic plant, the expression of the nucleic acids of the present invention.

Therefore, in one aspect, the present invention relates to an isolated nucleic acid comprising a member selected from the group consisting of (a) a polynucleotide having a specified sequence identity to a polynucleotide encoding a polypeptide of the present invention; (b) a polynucleotide which is complementary to the polynucleotide of (a); and, (c) a polynucleotide comprising a specified number of contiguous nucleotides from a polynucleotide of (a) or (b). The isolated nucleic acid can be DNA.

In another aspect, the present invention relates to recombinant expression cassettes, comprising a nucleic acid of the present invention operably linked to a promoter.

In another aspect, the present invention is directed to a host cell into which has been introduced the recombinant expression cassette.

In a further aspect, the present invention relates to an isolated protein comprising a polypeptide having a specified number of contiguous amino acids encoded by an isolated nucleic acid of the present invention.

In another aspect, the present invention relates to an isolated nucleic acid comprising a polynucleotide of specified length which selectively hybridizes under stringent conditions to a polynucleotide of the present invention, or a complement thereof. In some embodiments, the isolated nucleic acid is operably linked to a promoter.

In another aspect, the present invention relates to a recombinant expression cassette comprising a nucleic acid amplified from a library as referred to supra, wherein the nucleic acid is operably linked to a promoter. In some embodiments, the present invention relates to a host cell transfected with this recombinant expression cassette. In some embodiments, the present invention relates to a protein of the present invention that is produced from this host cell.

In yet another aspect, the present invention relates to a transgenic plant comprising a recombinant expression cassette comprising a plant promoter operably linked to any of the isolated nucleic acids of the present invention. The present invention also provides transgenic seed from the transgenic plant.

Definitions

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms ($5^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substances capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246:

1275–1281 (1989); and Ward et al., *Nature* 341: 544–546 (1989); and Vaughan et al., *Nature Biotech.* 14: 309–314 (1996).

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum,* or the ciliate *Macronucleus,* may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res*. 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual,* Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN <u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli,* or eukaryotic cells such as yeast, insect, amphibian, or mammalian cells.

Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

By "immunologically reactive conditions" or "immunoreactive conditions" is meant conditions which allow an antibody, reactive to a particular epitope, to bind to that epitope to a detectably greater degree (e.g., at least 2-fold over background) than the antibody binds to substantially any other epitopes in a reaction mixture comprising the particular epitope. Immunologically reactive conditions are dependent upon the format of the antibody binding reaction and typically are those utilized in immunoassay protocols. See Harlow and Lane, Antibodies, A Laboratory Manual, Cold Spring Harbor Publications, New York (1988), for a description of immunoassay formats and conditions.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The terms "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "maize RAD51 nucleic acid" is a nucleic acid of the present invention and means a nucleic acid comprising a polynucleotide of the present invention (a "maize RAD51 polynucleotide") encoding a maize RAD51 polypeptide. A "maize RAD51 gene" is a gene of the present invention and refers to a heterologous genomic form of a full-length maize RAD51 polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning-A Laboratory Manual,* 2nd ed., Vol. 1–3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants. A particularly preferred plant is *Zea mays.*

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether nor not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The term "maize RAD51 polypeptide" is a polypeptide of the present invention and refers to one or more amino acid sequences, in glycosylated or non-glycosylated form. The term is also inclusive of fragments, variants, homologs, alleles or precursors (e.g., preproproteins or proproteins) thereof. A "maize RAD51 protein" is a protein of the present invention and comprises a maize RAD51 polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "specifically reactive" includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Thus, under designated immunoassay conditions, the specified antibodies bind to an analyte having the recognized epitope to a substantially greater degree (e.g., at least 2-fold over background) than to substantially all analytes lacking the epitope which are present in the sample.

Specific binding to an antibody under such conditions may require an antibody that is selected for its specificity for a particular protein. For example, antibodies raised to the polypeptides of the present invention can be selected from to obtain antibodies specifically reactive with polypeptides of the present invention. The proteins used as immunogens can be in native conformation or denatured so as to provide a linear epitope.

A variety of immunoassay formats may be used to select antibodies specifically reactive with a particular protein (or other analyte). For example, solid-phase ELISA immunoassays are routinely used to select monoclonal antibodies specifically immunoreactive with a protein. See Harlow and Lane, *Antibodies, A Laboratory Manual,* Cold Spring Harbor Publications, New York (1988), for a description of immunoassay formats and conditions that can be used to determine selective reactivity.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.* 138: 267–284 (1984): $T_m=81.5°$ C.$+16.6$ (log M)$+0.41$ (%GC)$-0.61$ (% form)$-500/L$; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2: 482 (1981); by the homology alignment algorithm of Needleman and Wunsch, *J. Mol. Biol.* 48: 443 (1970); by the search for similarity method of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package (Accelrys, San Diego, Calif.); the CLUSTAL program is well described by Higgins and Sharp, *Gene* 73: 237–244 (1988); Higgins and Sharp, CABIOS 5: 151–153 (1989); Corpet et al., *Nucleic Acids Research* 16: 10881–90 (1988); Huang et al., *Computer Applications in the Biosciences* 8: 155–65 (1992), and Pearson et al., *Methods in Molecular Biology* 24: 307–331 (1994).

The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel et al., Eds., Greene Publishing and Wiley-Interscience, New York (1995).

Software for performing BLAST analyses is publicly available, e.g., through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89: 10915).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873–5877 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.* 17: 191–201 (1993)) low-complexity filters can be employed alone or in combination.

GAP can also be used to compare a polynucleotide or polypeptide of the present invention with a reference sequence. GAP uses the algorithm of Needleman and Wunsch (*J. Mol. Biol.* 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can each independently be: 0, 1, 2, 3, 4, 5, 6, 7, 8, 9, 10, 15, 20, 30, 40, 50, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) *Proc. Natl. Acad. Sci. USA* 89: 10915).

Unless otherwise stated, sequence identity/similarity values provided herein refer to the value obtained using the BLAST 2.0 suite of programs using default parameters (Altschul et al., *Nucleic Acids Res.* 25:3389–3402, 1997; Altschul et al., J. Mol. Bio. 215: 403–410, 1990) or to the value obtained using the GAP program using default parameters (see the Wisconsin Genetics Software Package GCG, Accelrys, San Diego, Calif.).

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE INVENTION

Overview

The present invention provides, among other things, compositions and methods for modulating (i.e., increasing or decreasing) the level of polynucleotides and polypeptides of the present invention in plants. In particular, the polynucleotides and polypeptides of the present invention can be expressed temporally or spatially, e.g., at developmental stages, in tissues, and/or in quantities, which are uncharacteristic of non-recombinantly engineered plants. Thus, the present invention provides utility in such exemplary applications as in the control of recombination efficiency or transformation efficiency in plants.

The present invention also provides isolated nucleic acid comprising polynucleotides of sufficient length and complementarity to a gene of the present invention to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms), orthologs, or paralogs of the gene, or for site directed mutagenesis in eukaryotic cells (see, e.g., U.S. Pat. No. 5,565,350). The isolated nucleic acids of the present invention can also be used for recombinant expression of their encoded polypeptides, or for use as immunogens in the preparation and/or screening of antibodies. The isolated nucleic acids of the present invention can also be employed for use in sense or antisense suppression of one or more genes of the present invention in a host cell, tissue, or plant. Attachment of chemical agents which bind, intercalate, cleave and/or crosslink to the isolated nucleic acids of the present invention can also be used to modulate transcription or translation.

The present invention also provides isolated proteins comprising a polypeptide of the present invention (e.g., preproenzyme, proenzyme, or enzymes). The present invention also provides proteins comprising at least one epitope from a polypeptide of the present invention. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, for identification of homologous polypeptides from other species, or for purification of polypeptides of the present invention.

The isolated nucleic acids and polypeptides of the present invention can be used over a broad range of plant types, particularly monocots such as the species of the family Gramineae including *Hordeum, Secale, Triticum, Sorghum*

(e.g., *S. bicolor*), *Oryza*, *Avena*, and *Zea* (e.g., *Z. mays*). The isolated nucleic acid and proteins of the present invention can also be used in species from the genera: *Cucurbita*, *Rosa*, *Vitis*, *Juglans*, *Fragaria*, *Lotus*, *Medicago*, *Onobrychis*, *Trifolium*, *Trigonella*, *Vigna*, *Citrus*, *Linum*, *Geranium*, *Manihot*, *Daucus*, *Arabidopsis*, *Brassica*, *Raphanus*, *Sinapis*, *Atropa*, *Capsicum*, *Datura*, *Hyoscyamus*, *Lycopersicon*, *Nicotiana*, *Solanum*, *Petunia*, *Digitalis*, *Majorana*, *Ciahorium*, *Helianthus*, *Lactuca*, *Bromus*, *Asparagus*, *Antirrhinum*, *Heterocallis*, *Nemesis*, *Pelargonium*, *Panieum*, *Pennisetum*, *Ranunculus*, *Senecio*, *Salpiglossis*, *Cucumis*, *Browaalia*, *Glycine*, *Pisum*, *Phaseolus*, and *Lolium*.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:

(a) a polynucleotide encoding a polypeptide of SEQ ID NOS: 2, 4, 6 and conservatively modified and polymorphic variants thereof, including exemplary polynucleotides of SEQ ID NOS: 1, 3, 5; polynucleotide sequences of the invention also include the maize RAD51 polynucleotide sequences as contained in plasmids deposited with American Type Culture Collection (ATCC) and assigned Accession Number 207181.

(b) a polynucleotide which is the product of amplification from a *Zea mays* nucleic acid library using primer pairs which selectively hybridize under stringent conditions to loci within a polynucleotide selected from the group consisting of SEQ ID NOS: 1, 3, 5, or the sequences as contained in the ATCC deposit assigned Accession No. 207181, wherein the polynucleotide has substantial sequence identity to a polynucleotide selected from the group consisting of SEQ ID NOS: 1, 3, and 5; or the sequences as contained in the ATCC deposit assigned Accession No. 207181.

(c) a polynucleotide which selectively hybridizes to a polynucleotide of (a) or (b);

(d) a polynucleotide having a specified sequence identity with polynucleotides of (a), (b), or (c);

(e) a polynucleotide encoding a protein having a specified number of contiguous amino acids from a prototype polypeptide, wherein the protein is specifically recognized by antisera elicited by presentation of the protein and wherein the protein does not detectably immunoreact to antisera which has been fully immunosorbed with the protein;

(f) complementary sequences of polynucleotides of (a), (b), (c), (d), or (e); and (g) a polynucleotide comprising at least a specific number of contiguous nucleotides from a polynucleotide of (a), (b), (c), (d), (e), or (f).

The polynucleotides of SEQ ID NOS: 1, 3, and 5 are contained in plasmids deposited with American Type Culture Collection (ATCC) on Mar. 31, 1999 and assigned Accession Number 207181. American Type Culture Collection is located at 10801 University Blvd., Manassas, Va. 20110–2209.

The ATCC deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. Section 112.

A. Polynucleotides Encoding A Polypeptide of the Present Invention or Conservatively Modified or Polymorphic Variants Thereof As indicated in (a), above, the present invention provides isolated nucleic acids comprising a polynucleotide of the present invention, wherein the polynucleotide encodes a polypeptide of the present invention, or conservatively modified or polymorphic variants thereof. Accordingly, the present invention includes polynucleotides of SEQ ID NOS: 1, 3, 5, and the sequences as contained in the ATCC deposit assigned Accession No. 207181 and silent variations of polynucleotides encoding a polypeptide of SEQ ID NOS: 2, 4, 6. The present invention further provides isolated nucleic acids comprising polynucleotides encoding conservatively modified variants of a polypeptide of SEQ ID NOS: 2, 4, 6. Conservatively modified variants can be used to generate or select antibodies immunoreactive to the non-variant polypeptide. Additionally, the present invention further provides isolated nucleic acids comprising polynucleotides encoding one or more allelic (polymorphic) variants of polypeptides/polynucleotides. Polymorphic variants are frequently used to follow segregation of chromosomal regions in, for example, marker assisted selection methods for crop improvement.

B. Polynucleotides Amplified from a *Zea mays* Nucleic Acid Library

As indicated in (b), above, the present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23, and Mo17 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, S. *Gene* 138: 171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371, 1995). cDNA synthesis is often catalyzed at 50–55° C. to prevent formation of RNA secondary structure. Examples of reverse transcriptases that are relatively stable at these temperatures are SUPERSCRIPT II Reverse Transcriptase (Life Technologies, Inc.), AMV Reverse Transcriptase (Boehringer Mannheim) and RETROAMP Reverse Transcriptase (Epicentre). Rapidly growing tissues, or rapidly dividing cells are preferably used as mRNA sources.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid which they amplify. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes which are specific to a polypeptide of the present invention. Methods for protein synthesis from PCR derived templates are known in the art and available commercially. See, e.g., Amersham Life Sciences, Inc, Catalog '97, p. 354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel et al., Eds, Greene Publishing and Wiley-Interscience, New York (1995); Frohman and Martin, *Techniques* 1:165 (1989).

C. Polynucleotides Which Selectively Hybridize to a Polynucleotide of (A) or (B)

As indicated in (c), above, the present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: corn, canola, soybean, cotton, wheat, sorghum, sunflower, oats, sugar cane, millet, barley, and rice. Optionally, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

As indicated in (d), above, the present invention provides isolated nucleic acids comprising polynucleotides of the present invention, wherein the polynucleotides have a specified identity at the nucleotide level to a polynucleotide as disclosed above in sections (A), (B), or (C), above. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 81%, 82%, 83%, 84%, 85%, 86%, 87%, 88%, 89%, 90%, 91%, 92%, 93%, 94%, 95%, 96%, 97%, 98%, or 99%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Nos. 91/17271, 91/18980, 91/19818, and 93/08278. Other systems for generating libraries of peptides have aspects of both in vitro chemical synthesis and recombinant methods. See, PCT Patent publication Nos. 92/05258, 92/14843, and 96/19256. See also, U.S. Pat. Nos. 5,658,754 and 5,643,768. Peptide display libraries, vectors, and screening kits are commercially available from such suppliers as Invitrogen (Carlsbad, Calif.).

E. Polynucleotides Encoding a Protein Having a Subsequence from a Prototype Polypeptide and is Cross-Reactive to the Prototype Polypeptide As indicated in (e), above, the present invention provides isolated nucleic acids comprising polynucleotides of the present invention, wherein the polynucleotides encode a protein having a subsequence of contiguous amino acids from a prototype polypeptide of the present invention such as are provided in (a), above. The length of contiguous amino acids from the prototype polypeptide is selected from the group of integers consisting of from at least 10 to the number of amino acids within the prototype sequence. Thus, for example, the polynucleotide can encode a polypeptide having a subsequence having at least 10, 15, 20, 25, 30, 35, 40, 45, or 50, contiguous amino acids from the prototype polypeptide. Further, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The proteins encoded by polynucleotides of this embodiment, when presented as an immunogen, elicit the production of polyclonal antibodies which specifically bind to a prototype polypeptide such as but not limited to, a polypeptide encoded by the polynucleotide of (a) or (b), above. Generally, however, a protein encoded by a polynucleotide of this embodiment does not bind to antisera raised against the prototype polypeptide when the antisera has been fully immunosorbed with the prototype polypeptide. Methods of making and assaying for antibody binding specificity/affinity are well known in the art. Exemplary immunoassay formats include ELISA, competitive immunoassays, radioimmunoassays, Western blots, indirect immunofluorescent assays and the like.

In a preferred assay method, fully immunosorbed and pooled antisera which is elicited to the prototype polypeptide can be used in a competitive binding assay to test the protein. The concentration of the prototype polypeptide required to inhibit 50% of the binding of the antisera to the prototype polypeptide is determined. If the amount of the protein required to inhibit binding is less than twice the amount of the prototype protein, then the protein is said to specifically bind to the antisera elicited to the immunogen. Accordingly, the proteins of the present invention embrace allelic variants, conservatively modified variants, and minor recombinant modifications to a prototype polypeptide.

A polynucleotide of the present invention optionally encodes a protein having a molecular weight as the non-glycosylated protein within 20% of the molecular weight of the full-length non-glycosylated polypeptides of the present invention. Molecular weight can be readily determined by SDS-PAGE under reducing conditions. Optionally, the molecular weight is within 15% of a full length polypeptide of the present invention, more preferably within 10% or 5%, and most preferably within 3%, 2%, or 1% of a full length polypeptide of the present invention.

Optionally, the polynucleotides of this embodiment will encode a protein having a specific enzymatic activity at least 50%, 60%, 80%, or 90% of a cellular extract comprising the native, endogenous full-length polypeptide of the present invention. Further, the proteins encoded by polynucleotides of this embodiment will optionally have a substantially similar affinity constant ($K_m$) and/or catalytic activity (i.e., the microscopic rate constant, $k_{cat}$) as the native endogenous, full-length protein. Those of skill in the art will recognize that $k_{cat}/K_m$ value determines the specificity for competing substrates and is often referred to as the specificity constant. Proteins of this embodiment can have a $k_{cat}/K_m$ value at least 10% of a full-length polypeptide of the present invention as determined using the endogenous substrate of that polypeptide. Optionally, the $k_{cat}/K_m$ value will be at least 20%, 30%, 40%, 50%, and most preferably at least 60%, 70%, 80%, 90%, or 95% the $k_{cat}/K_m$ value of the full-length polypeptide of the present invention. Determination of $k_{cat}$, $K_m$, and $k_{cat}/K_m$ can be determined by any number of means well known to those of skill in the art. For example, the initial rates (i.e., the first 5% or less of the reaction) can be determined using rapid mixing and sampling techniques (e.g., continuous-flow, stopped-flow, or rapid quenching techniques), flash photolysis, or relaxation methods (e.g., temperature jumps) in conjunction with such exemplary methods of measuring as spectrophotometry, spectrofluorimetry, nuclear magnetic resonance, or radioactive procedures. Kinetic values are conveniently obtained using a Lineweaver-Burk or Eadie-Hofstee plot.

F. Polynucleotides Complementary to the Polynucleotides of (A)–(E)

As indicated in (f), above, the present invention provides isolated nucleic acids comprising polynucleotides complementary to the polynucleotides of paragraphs A–E, above. As those of skill in the art will recognize, complementary sequences base-pair throughout the entirety of their length with the polynucleotides of sections (A)–(E) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

G. Polynucleotides Which are Subsequences of the Polynucleotides of (A)–(F)

As indicated in (g), above, the present invention provides isolated nucleic acids comprising polynucleotides which comprise at least 15 contiguous bases from the polynucleotides of sections (A) through (F) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 35, 40, 45, 50, 55, 60, 65, 70, 75, 80, 85, 90 or 100 contiguous nucleotides in length from the polynucleotides of (A)–(F). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is Zea mays.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. A polynucleotide of the present invention can be attached to a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known and extensively described in the art. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a CDNA or genomic DNA library. While isolation of RNA, and construction of CDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of organelles and proteins, followed by precipitation of nucleic acids. Extraction of total RNA from plant cells can be accomplished by a variety of means. Frequently, extraction buffers include a strong detergent such as SDS and an organic denaturant such as guanidinium isothiocyanate, guanidine hydrochloride or phenol. Following total RNA isolation, poly(A)$^+$mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5'-3' (Paoli Inc., Pa.). See also, U.S. Pat. Nos. 5,614,391 and 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)$^+$mRNA template using a poly(dT) primer or random hexanucleotides. Second, the resultant RNA-DNA hybrid is converted into double stranded cDNA, typically by reaction with a combination of RNAse H and DNA polymerase I (or Klenow fragment). Third, the termini of the double stranded CDNA are ligated to adaptors. Ligation of the adaptors can produce cohesive ends for cloning. Fourth, size selection of the double stranded cDNA eliminates excess adaptors and primer fragments, and eliminates partial cDNA molecules due to degradation of mRNAs or the failure of reverse transcriptase to synthesize complete first strands. Fifth, the cDNAs are ligated into cloning vectors and packaged. cDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel et al., Eds., Greene Publishing and Wiley-Interscience, New York (1995). cDNA synthesis kits are available from a variety of commercial vendors such as Stratagene or Pharmacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Carninci et al., Genomics 37: 327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.* 15(6): 3363–3371 (1995); and, PCT Application WO 96/34981.

A3. Normalized or Subtracted CDNA Libraries

A non-normalized CDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res*. 18(19): 5705–5711 (1990); Patanjali et al., *Proc. Natl. Acad. USA*. 88:1943–1947 (1991); U.S. Pat. Nos. 5,482,685 and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA* 91: 9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized cDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2): 58–63 (1991); Sive and St. John, *Nucl. Acids Res.*, 16(22): 10937 (1988); *Current Protocols in Molecular Biology*, Ausubel et al., Eds., Greene Publishing and Wiley-Interscience, New York (1995); and, Swaroop et al., *Nucl. Acids Res*. 19(8): 1954 (1991). cDNA subtraction kits are commercially available. See, e.g., PCR-Select (Clontech, Palo Alto, Calif.).

A4. Construction of a Genomic Library

To construct genomic libraries, large segments of genomic DNA are generated by fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, *PCR Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques* 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, above.

B. Synthetic Methods for Constructing Nucleic Acids

The isolated nucleic acids of the present invention can also be prepared by direct chemical synthesis by methods such as the phosphotriester method of Narang et al., *Meth. Enzymol*. 68: 90–99 (1979); the phosphodiester method of Brown et al., *Meth. Enzymol*. 68: 109–151 (1979); the diethylphosphoramidite method of Beaucage et al., *Tetra. Letts*. 22: 1859–1862 (1981); the solid phase phosphoramidite triester method described by Beaucage and Caruthers, *Tetra. Letts*. 22(20): 1859–1862 (1981), e.g., using an automated synthesizer, e.g., as described in Needham-VanDevanter et al., *Nucleic Acids Res*. 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is best employed for sequences of about 100 bases or less, longer sequences may be obtained by the ligation of shorter sequences.

Recombinant Expression Cassettes

The present invention further provides recombinant expression cassettes comprising a nucleic acid of the present invention. A nucleic acid sequence coding for the desired polypeptide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/selective expression), a transcription initiation start site, a ribosome binding site, an RNA processing signal, a transcription termination site, and/or a polyadenylation signal.

A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter, and other transcription initiation regions from various plant genes known to those of skill. One exemplary promoter is the ubiquitin promoter, which can be used to drive expression of the present invention in maize embryos or embryogenic callus.

Alternatively, the plant promoter can direct expression of a polynucleotide of the present invention in a specific tissue or may be otherwise under more precise environmental or developmental control. Such promoters are referred to here as "inducible" promoters. Environmental conditions that may effect transcription by inducible promoters include pathogen attack, anaerobic conditions, or the presence of light. Examples of inducible promoters are the Adh1 promoter which is inducible by hypoxia or cold stress, the Hsp70 promoter which is inducible by heat stress, and the PPDK promoter which is inducible by light.

Examples of promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. The operation of a promoter may also vary depending on its location in the genome. Thus, an inducible promoter may become fully or partially constitutive in certain locations.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in *Zea mays*, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

Methods for identifying promoters with a particular expression pattern, in terms of, e.g., tissue type, cell type, stage of development, and/or environmental conditions, are well known in the art. See, e.g., *The Maize Handbook*, Chapters 114–115, Freeling and Walbot, Eds., Springer, N.Y. (1994); *Corn and Corn Improvement*, $3^{rd}$ edition, Chapter 6, Sprague and Dudley, Eds., American Society of Agronomy, Madison, Wis. (1988). A typical step in promoter isolation methods is identification of gene products that are expressed with some degree of specificity in the target tissue. Amongst the range of methodologies are: differential hybridization to cDNA libraries; subtractive hybridization; differential display; differential 2-D protein gel electrophoresis; DNA probe arrays; and isolation of proteins known to be expressed with some specificity in the target tissue. Such methods are well known to those of skill in the art. Commercially available products for identifying promoters are known in the art such as Clontech's (Palo Alto, Calif.) Universal GenomeWalker Kit.

For the protein-based methods, it is helpful to obtain the amino acid sequence for at least a portion of the identified protein, and then to use the protein sequence as the basis for preparing a nucleic acid that can be used as a probe to identify either genomic DNA directly, or preferably, to identify a cDNA clone from a library prepared from the target tissue. Once such a cDNA clone has been identified, that sequence can be used to identify the sequence at the 5' end of the transcript of the indicated gene. For differential hybridization, subtractive hybridization and differential display, the nucleic acid sequence identified as enriched in the target tissue is used to identify the sequence at the 5' end of the transcript of the indicated gene. Once such sequences are identified, starting either from protein sequences or nucleic acid sequences, any of these sequences identified as being from the gene transcript can be used to screen a genomic library prepared from the target organism. Methods for identifying and confirming the transcriptional start site are well known in the art.

In the process of isolating promoters expressed under particular environmental conditions or stresses, or in specific tissues, or at particular developmental stages, a number of genes are identified that are expressed under the desired circumstances, in the desired tissue, or at the desired stage. Further analysis will reveal expression of each particular gene in one or more other tissues of the plant. One can identify a promoter with activity in the desired tissue or condition but that does not have activity in any other common tissue.

To identify the promoter sequence, the 5' portions of the clones described here are analyzed for sequences characteristic of promoter sequences. For instance, promoter sequence elements include the TATA box consensus sequence (TATAAT), which is usually an AT-rich stretch of 5–10 bp located approximately 20 to 40 base pairs upstream of the transcription start site. Identification of the TATA box is well known in the art. For example, one way to predict the location of this element is to identify the transcription start site using standard RNA-mapping techniques such as primer extension, S1 analysis, and/or RNase protection. To confirm the presence of the AT-rich sequence, a structure-function analysis can be performed involving mutagenesis of the putative region and quantification of the mutation's effect on expression of a linked downstream reporter gene. See, e.g., *The Maize Handbook*, Chapter 114, Freeling and Walbot, Eds., Springer, N.Y., (1994).

In plants, further upstream from the TATA box, at positions −80 to −100, there is typically a promoter element (i.e., the CAAT box) with a series of adenines surrounding the trinucleotide G (or T) N G. J. Messing et al., in *Genetic Engineering in Plants*, Kosage, Meredith and Hollaender, Eds., pp. 221–227 (1983). In maize, there is no well conserved CAAT box but there are several short, conserved protein-binding motifs upstream of the TATA box. These include motifs for the trans-acting transcription factors involved in light regulation, anaerobic induction, hormonal regulation, or anthocyanin biosynthesis, as appropriate for each gene.

Once promoter and/or gene sequences are known, a region of suitable size is selected from the genomic DNA that is 5' to the transcriptional start, or the translational start site, and such sequences are then linked to a coding sequence. If the transcriptional start site is used as the point of fusion, any of a number of possible 5' untranslated regions can be used in between the transcriptional start site and the partial coding sequence. If the translational start site at the 3' end of the specific promoter is used, then it is linked directly to the methionine start codon of a coding sequence.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchman and Berg, *Mol. Cell Biol.* 8: 4395–4405 (1988); Callis et al., *Genes Dev.* 1: 1183–1200 (1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. in Enzymol. 153: 253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., Gene 61: 1–11 (1987) and Berger et al., Proc. Natl. Acad. Sci. USA 86: 8402–8406 (1989). Another useful vector herein is plasmid pBl101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al., *Proc. Nat'l. Acad. Sci. USA* 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups-on polynucleotides of the present invention can be used to bind, label, detect, and/or cleave nucleic acids. For example, Vlassov, V. V., et al., *Nucleic Acids Res* (1986) 14: 4065–4076, describe covalent bonding of a single-stranded DNA fragment with alkylating derivatives of nucleotides complementary to target sequences. A report of similar work by the same group is that by Knorre, D. G., et al., *Biochimie* (1985) 67: 785–789. Iverson and Dervan also showed sequence-specific cleavage of single-stranded DNA mediated by incorporation of a modified nucleotide which was capable of activating cleavage (*J Am Chem Soc* (1987) 109:1 241–1243). Meyer, R. B., et al., *J Am Chem Soc* (1989) 111: 8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27: 3197–3203. Use of crosslinking in triple-helix forming probes was also disclosed by Home et al., *J Am Chem Soc* (1990) 112: 2435–2437. Use of N4, N4-ethanocytosine as an alkylating agent to crosslink to single-stranded oligonucleotides has also been described by Webb and Matteucci, *J Am Chem Soc* (1986) 108:2 764–2765; *Nucleic Acids Res* (1986) 14: 7661–7674; Feteritz et al., *J. Am. Chem. Soc.* 113: 4000 (1991). Various compounds to bind, detect, label, and/or cleave nucleic acids are known in the art. See, for example, U.S. Pat. Nos. 5,543,507; 5,672,593; 5,484,908; 5,256,648 and, 5,681,941.

Proteins

The isolated proteins of the present invention comprise a polypeptide having at least 10 amino acids encoded by any one of the polynucleotides of the present invention as discussed more fully, above, or polypeptides which are conservatively modified variants thereof. The proteins of the present invention or variants thereof can comprise any number of contiguous amino acid residues from a polypeptide of the present invention, wherein that number is selected from the group of integers consisting of from 10 to the number of residues in a full-length polypeptide of the present invention. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

The present invention further provides a protein comprising a polypeptide having a specified sequence identity with a polypeptide of the present invention. The percentage of sequence identity is an integer selected from the group consisting of from 50 to 99. Exemplary sequence identity values include 60%, 65%, 70%, 75%, 80%, 85%, 86%, 87%, 88%, 89%, 90%, 91%, 92%, 93%, 94%, 95%, 96%, 97%, 98% and 99%. Sequence identity can be determined using, for example, the GAP or BLAST algorithms.

As those of skill will appreciate, the present invention includes catalytically active polypeptides of the present invention (i.e., enzymes). Catalytically active polypeptides have a specific activity of at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity.

Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located purification sequences. Restriction sites or termination codons can also be introduced.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198: 1056 (1977)), the tryptophan (trp) promoter system (Goeddel et al., *Nucleic Acids Res*. 8: 4057 (1980)) and the lambda derived P L promoter and N-gene ribosome binding site (Shimatake et al., *Nature* 292: 128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using *Bacillus sp.* and *Salmonella* (Palva et al., *Gene* 22: 229–235 (1983); Mosbach et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Two widely utilized yeast for production of eukaryotic proteins are *Saccharomyces cerevisiae* and *Pichia pastoris*. Vectors, strains, and protocols for expression in *Saccharomyces* and *Pichia* are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol*. Rev. 89: 49 (1986)), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, *J. Embryol. Exp. Morphol*. 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague et al., *J. Virol*. 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in DNA Cloning Vol. II a Practical Approach, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for effective transformation/transfection may be employed.

A. Plant Transformation

A DNA sequence coding for the desired polynucleotide of the present invention, for example a cDNA or a genomic sequence encoding a full length protein, will be used to construct a recombinant expression cassette which can be introduced into the desired plant.

Isolated nucleic acids of the present invention can be introduced into plants according to techniques known in the art. Generally, recombinant expression cassettes as described above and suitable for transformation of plant cells are prepared. The isolated nucleic acids of the present invention can then be used for transformation. In this manner, genetically modified plants, plant cells, plant tissue, seed, and the like can be obtained. Transformation protocols may vary depending on the type of plant cell, i.e. monocot or dicot, targeted for transformation. Suitable methods of transforming plant cells include microinjection (Crossway et al. (1986) Biotechniques 4:320–334), electroporation (Riggs et al (1986) *Proc. Natl. Acad. Sci. USA* 83:5602–5606, *Agrobacterium* mediated transformation (see for example, Zhao et al. U.S. Pat. No. 5,981,840; Hinchee et al. (1988) *Biotechnology* 6:915–921), direct gene transfer (Paszkowski et al (1984) EMBO J. 3:2717–2722), and ballistic particle acceleration (see, for example, Sanford et al. U.S. Pat. No. 4,945,050; Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995); and McCabe et al. (1988) *Biotechnology* 6:923–926). Also see, Weissinger et al. (1988) *Annual Rev. Genet* 22:421477; Sanford et al. (1987) *Particulate Science and Technology* 5:27–37 (onion); Christou et al. (1988) *Plant Phisiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes et al. "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995) (maize); Klein et al. (1988) *Plant Physiol.* 91:440–444 (maize) Fromm et al. (1990) *Biotechnology* 8:833–839 (maize); Hooykaas-Van Slogteren & Hooykaas (1984) *Nature (London)* 311:763–764; Bytebier et al. (1987) *Proc. Natl. Acad. Sci. USA* 84:5345–5349 (Liliaceae); De Wet et al. (1985) In *The Experimental Manipulation of Ovule Tissues* ed. G. P. Chapman et al. pp. 197–209. Longman, N.Y. (pollen); Kaeppler et al. (1990) *Plant Cell Reports* 9:415–418; and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:745–750 (maize via *Agrobacterium tumefaciens*); all of which are herein incorporated by reference.

The cells which have been transformed may be grown into plants in accordance with conventional ways. See, for example, McCormick et al. (1986) Plant *Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

B. Transfection of Prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis*, Part A.; Merrifield et al., *J. Am. Chem. Soc.* 85: 2149–2156 (1963), and *Stewart* et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fusion protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including detergent solubilization, selective precipitation with such substances as ammonium sulfate, column chromatography, immunopurification methods, and others. See, for instance, R. Scopes, *Protein Purification: Principles and Practice*, Springer-Verlag: New York (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Transgenic Plant Regeneration

Plants cells transformed with a plant expression vector can be regenerated, e.g., from single cells, callus tissue or leaf discs according to standard plant tissue culture techniques. It is well known in the art that various cells, tissues, and organs from almost any plant can be successfully cultured to regenerate an entire plant. Plant regeneration from cultured protoplasts is described in Evans et al., *Protoplasts Isolation and Culture, Handbook of Plant Cell Culture*, Macmillilan Publishing Company, New York, pp. 124–176 (1983); and Binding, *Regeneration of Plants, Plant Protoplasts*, CRC Press, Boca Raton, pp. 21–73 (1985).

The regeneration of plants containing the foreign gene introduced by *Agrobacterum* from leaf explants can be achieved as described by Horsch et al., *Science*, 227:1229–1231 (1985). In this procedure, transformants are grown in the presence of a selection agent and in a medium that induces the regeneration of shoots in the plant species being transformed as described by Fraley et al., *Proc. Natl. Acad. Sci. (U.S.A.)*, 80:4803 (1983). This procedure typically produces shoots within two to four weeks and these transformant shoots are then transferred to an appropriate root-inducing medium containing the selective agent and an antibiotic to prevent bacterial growth. Transgenic plants of the present invention may be fertile or sterile.

Regeneration can also be obtained from plant callus, explants, organs, or parts thereof. Such regeneration techniques are described generally in Klee et al., *Ann. Rev. of Plant Phys.* 38: 467–486 (1987). The regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process includes the steps of selection of transformant cells and shoots, rooting the transformant shoots and growth of the plantlets in soil. For maize cell culture and regeneration see generally, *The Maize Handbook*, Freeling and Walbot, Eds., Springer, N.Y. (1994); *Corn and Corn Improvement*, $3^{rd}$ edition, Sprague and Dudley Eds., American Society of Agronomy, Madison, Wis. (1988).

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

Transgenic plants expressing the selectable marker can be screened for transmission of the nucleic acid of the present invention by, for example, standard immunoblot and DNA detection techniques. Transgenic lines are also typically evaluated on levels of expression of the heterologous nucleic acid. Expression at the RNA level can be determined initially to identify and quantitate expression-positive plants. Standard techniques for RNA analysis can be employed and include PCR amplification assays using oligonucleotide primers designed to amplify only the heterologous RNA templates and solution hybridization assays using heterologous nucleic acid-specific probes. The RNA-positive plants can then analyzed for protein expression by Western immunoblot analysis using the specifically reactive antibodies of the present invention. In addition, in situ hybridization and immunocytochemistry according to standard protocols can be done using heterologous nucleic acid specific polynucleotide probes and antibodies, respectively, to localize sites of expression within transgenic tissue. Generally, a number of transgenic lines are usually screened for the incorporated nucleic acid to identify and select plants with the most appropriate expression profiles.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non-transgenic plant are also contemplated.

Modulating Polypeptide Levels and/or Composition

The present invention further provides a method for modulating (i.e., increasing or decreasing) the concentration or ratio of the polypeptides of the present invention in a plant or part thereof. Modulation can be effected by increasing or decreasing the concentration and/or the ratio of the polypeptides of the present invention in a plant.

The method comprises introducing into a plant cell with a recombinant expression cassette comprising a polynucleotide of the present invention as described above to obtain a transformed plant cell, culturing the transformed plant cell under plant cell growing conditions, and inducing or repressing expression of a polynucleotide of the present invention in the plant for a time sufficient to modulate concentration and/or the ratios of the polypeptides in the plant or plant part.

In some embodiments, the concentration and/or ratios of polypeptides of the present invention in a plant may be modulated by altering, in vivo or in vitro, the promoter of a gene to up- or down-regulate gene expression. In some embodiments, the coding regions of native genes of the present invention can be altered via substitution, addition, insertion, or deletion to decrease activity of the encoded enzyme. See, e.g., Kmiec, U.S. Pat. No. 5,565,350; Zarling et al., PCT/US93/03868. And in some embodiments, an isolated nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate the concentration and/or ratios of polypeptides of the present invention in the plant. Plant forming conditions are well known in the art and discussed briefly, supra.

In general, concentration or the ratios of the polypeptides is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, the polypeptides of the present invention are modulated in monocots, particularly maize.

Molecular Markers

The present invention provides a method of genotyping a plant comprising a polynucleotide of the present invention. Optionally, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp. 7–21.

The particular method of genotyping in the present invention may employ any number of molecular marker analytic techniques such as, but not limited to, restriction fragment length polymorphisms (RFLPs). RFLPs are the product of allelic differences between DNA restriction fragments resulting from nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a gene of the present invention.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or restriction-enzyme treated (e.g., Pst I) genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCA); 2) denaturing gradient gel electrophoresis (DGGE); 3) RNase protection assays; 4) allele-specific oligonucleotides (ASOs); 5) the use of proteins which recognize nucleotide mismatches, such as the *E. coli* mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTRs and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res*.15:8125 (1987)) and the 7-methylguanosine cap structure (Drummond et al., *Nucleic Acids Res*. 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol*. 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host such as to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res*. 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication No. WO 97/20078. See also, Zhang, J.- H., et al. *Proc. Natl. Acad. Sci. USA* 94:4504–4509 (1997). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be a decreased $K_m$ and/or increased $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide, sequence, respectively. The individual species encompassed by a polynucleotide having an amino acid or nucleic acid consensus sequence can be used to generate antibodies or produce nucleic acid probes or primers to screen for homologs in other species, genera, families, orders, classes, phylums, or kingdoms. For example, a polynucleotide having a consensus sequences from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length polypeptide of the present invention (e.g., enzyme). Generally, the polypeptide will be present in a range sufficient to determine the effect of the compound, typically about 1 nM to 10 µM. Likewise, the compound will be present in a concentration of from about 1 nM to 10 µM. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, $2^{nd}$ ed., John Wiley and Sons, New York (1976).

Although the present invention has been described in some detail by way of illustration and example for purposes of clarity of understanding, it will be obvious that certain changes and modifications may be practiced within the scope of the appended claims.

EXAMPLE 1

This example describes the construction of the cDNA libraries.

Total RNA Isolation

The RNA for SEQ ID NO: 1 was isolated from pooled stem tissue of a B73 maize line sampled at night at the V8 to V12 stage and collected from the 4 to 5 internodes subtending the tassel. Tissue collected from B73 maize line seedlings following a 10 day drought and a heat shock of 24 hours was the source of RNA for SEQ ID NO: 3. The polyA RNA used to prepare the library for SEQ ID NO: 5 was prepared from pedicels dissected 20 days after pollination in a B73 maize line. Total RNA was isolated from corn tissues with TRIZOL Reagent (Life Technology Inc. Gaithersburg, Md.) using a modification of the guanidine isothiocyanate/acid-phenol procedure described by Chomczynski and Sacchi (Chomczynski, P., and Sacchi, N. *Anal. Biochem.* 162, 156 (1987)). In brief, plant tissue samples were pulverized in liquid nitrogen before the addition of the TRIZOL Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+RNA Isolation

The selection of poly(A)+RNA from total RNA was performed using POLYATTRACT system (mRNA isolation system, Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringency conditions and eluted by RNase-free deionized water.

cDNA Library Construction cDNA synthesis was performed and unidirectional cDNA libraries were constructed using the SUPERSCRIPT Plasmid System (Life Technology Inc. Gaithersburg, Md.). The first stand of cDNA was synthesized by priming an oligo (dT) primer containing a Not I site. The reaction was catalyzed by SUPERSCRIPT Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by SEPHACRYL-S400 chromatography. The selected cDNA molecules were ligated into pSPORT1 vector in between of Not I and Sal I sites.

EXAMPLE 2

This example describes cDNA sequencing and library subtraction.

Sequencing Template Preparation

Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22 ×22 cm² agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22 ×22 cm² nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper pre-wetted with denaturing solution for four minutes, then were incubated on top of a boiling water bath for additional four minutes. The filters were then placed on filter paper pre-wetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., (in Molecular Cloning: A laboratory Manual, 2$^{nd}$ Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire corn sequence database.
4. A Sal-A20 oligo nucleotide: TCG ACC CAC GCG TCC GAA AAA AAA AAA AAA AAA AAA, listed in SEQ ID NO: 7, removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

This example describes identification of the gene from a computer homology search.

Gene identities were determined by conducting BLAST (Basic Local Alignment Search Tool; Altschul, S. F., et al., (1990) J. Mol. Biol. 215:403–410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. *Nature Genetics* 3:266–272 (1993)) provided by the NCBI. In some cases, the sequencing data from two or more clones containing overlapping segments of DNA were used to construct contiguous DNA sequences.

EXAMPLE 4

This example displays the comparison of the amino acid sequences of the novel maize Rad51 orthologue (SEQ ID NO: 2) and the *Arabidopsis thaliana* Rad51C-like orthologue (SEQ ID NO: 8, Accession No. AC002387, Locus AAB82635, GI: 2583126). The ATP binding motif (Walker A Box) is highlighted.

The sequence comparison was carried out using the BestFit program in GCG. The top line is the Arabidopsis sequence as exemplified in SEQ ID NO: 8. The bottom line is the maize sequence as exemplified in SEQ ID NO: 2.

The parameters of the BestFit program for the present calculation are as follows: Gap Weight:8; Average Match: 2.912; Length Weight:2; Average Mismatch: -2.003; Ratio: 3.623; Gaps:2; Percent Similarity:78.388; Percent Identity: 67.033

```
59  AKN AWD MLH EEE S L PR I TT S C S DL  DN ILGGG I S CRD VTE I GGVPG IGKT Q 108
    |.|||||   :| |    |||    ||..||||||  |::||||||||||:|||  |
19  AQN AWD MF S DELS QK H I TTG SG DL  ND ILGGG IH CKE VTE I G GVPGVGKT Q 68

109  IG IQ L SV NVQ IPR ECGGLGG K A I Y I DT EGSFMV ERA LQ I AE AC VEDMEE Y 158
     :||||.:||||| ||||||||||:|||||||||| ||||  |: |.  |:
69   LG IQ L A I NVQ IPV ECGGLGG K AVY I DT EGSFMV ERV YQ I AE GC IRD I LE H 118

159  TGY MH K HFQANQVQM KPED I L EN I FYFRVC SY T EQ I ALVNH LEKF I SEN K 208
     : |. . | |:.||  |.|:|||:|||||||.:|:  :|||: |.|
119  FPH S H E KS SSVQKQ LQPE R F LAD I YYFR IC SY T EQ I AV INY MEKFLREH K 168

209  DV . V V I VDSI T F HF RQDYDD LAQR TRV L SEMAL KFM KLAKK FS LAVVLL N 257
     || : || :||:|||||||::||| ||||| :.|| ||:|| :.||||||||
169  DVR I V I I DSVTF HF RQDFE D LAL R TRVLSG L S LKLM K IAKT YNLAVVLL N 218

258  QVT T K F SEG SFQL A LALGDSWS H S CTNRVI LYW NGDERY AY I DKS PSLP S 307
     ||||  || . ||||||  ||||||||||| |||.|| :| ||. |||| : :|||||||
219  QVTT  K F TEG SFQ L T LALGDSWS H S CTNRL ILHW NGNERY AH L DKS PSLP V 268

308  ASA S Y T VTSRGL RN S. S SS S KRV KM 331
     |||  |  ||  :|:|..  ||. ||  :.
269  ASA P Y A VTGKG I RDAVS SNH KRAR V 293
```

The above examples are provided to illustrate the invention but not to limit its scope. Other variants of the invention will be readily apparent to one of ordinary skill in the art and are encompassed by the appended claims. All publications, patents, patent applications, and computer programs cited herein are hereby incorporated by reference.

What is claimed is

1. An isolated polypeptide comprising an amino acid sequence having at least 80% sequence identity to over the entire length of SEQ ID NO: 2, wherein the amino acid sequence encodes a polypeptide which specifically binds XRCC3.

2. The polypeptide of claim 1 wherein the amino acid sequence has at least 85% sequence identity to SEQ ID NO: 2.

3. The polypeptide of claim 1 wherein the amino acid sequence has at least 90% sequence identity to SEQ ID NO: 2.

4. The polypeptide of claim 1 wherein the amino acid sequence has at least 95% sequence identity to SEQ ID NO: 2.

5. An isolated polypeptide comprising SEQ ID NO: 2.

6. An isolated polypeptide comprising an amino acid sequence having at least 80% sequence identity to over the entire length of SEQ ID NO: 2, wherein the amino acid sequence encodes a polypeptide which forms part of a recombinosome.

7. The polypeptide of claim 6 wherein the amino acid sequence has at least 85% sequence identity to SEQ ID NO: 2.

8. The polypeptide of claim 6 wherein the amino acid sequence has at least 90% sequence identity to SEQ ID NO; 2.

9. The polypeptide of claim 6 wherein the amino acid sequence has at least 95% sequence identity to SEQ ID NO: 2.

* * * * *